(12) United States Patent
Miki et al.

(10) Patent No.: US 8,053,092 B2
(45) Date of Patent: Nov. 8, 2011

(54) M-CARBAZOLYLPHENYL COMPOUNDS

(75) Inventors: Tetsuzo Miki, Minato-ku (JP);
Norimasa Yokoyama, Tsukuba (JP);
Shigeru Kusano, Tsukuba (JP);
Chihaya Adachi, Fukuoka (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 406 days.

(21) Appl. No.: 12/097,159

(22) PCT Filed: Dec. 12, 2006

(86) PCT No.: PCT/JP2006/324766
§ 371 (c)(1),
(2), (4) Date: Jun. 12, 2008

(87) PCT Pub. No.: WO2007/069607
PCT Pub. Date: Jun. 21, 2007

(65) Prior Publication Data
US 2009/0045726 A1    Feb. 19, 2009

(30) Foreign Application Priority Data
Dec. 12, 2005   (JP) .................. 2005-357634

(51) Int. Cl.
*H01L 51/54* (2006.01)
*H01J 1/63* (2006.01)
*C07D 403/10* (2006.01)
*C07D 403/12* (2006.01)

(52) U.S. Cl. ........ 428/690; 428/917; 313/504; 313/506; 548/440

(58) Field of Classification Search .................. None
See application file for complete search history.

(56) References Cited

U.S. PATENT DOCUMENTS

| 2001/0053462 A1* | 12/2001 | Mishima ................ 428/690 |
| 2005/0175858 A1* | 8/2005 | Jung et al. ............ 428/690 |
| 2006/0088728 A1* | 4/2006 | Kwong et al. ......... 428/690 |
| 2007/0015004 A1* | 1/2007 | Nariyuki .............. 428/690 |
| 2007/0104976 A1* | 5/2007 | Iwakuma et al. ....... 428/690 |

FOREIGN PATENT DOCUMENTS

| JP | 2002-241352 | | 8/2002 |
| JP | 2004-178896 | | 6/2004 |
| JP | 2005-132820 | | 5/2005 |
| JP | 2005-320277 | A * | 11/2005 |
| WO | WO 03/079736 | A1 | 9/2003 |
| WO | WO 2005/051046 | A1 | 6/2005 |
| WO | WO 2005/057987 | A1 * | 6/2005 |
| WO | WO 2006/062062 | A1 | 6/2006 |

OTHER PUBLICATIONS

M. A. Baldo, et al., "Very high-efficiency green organic light-emitting devices based on electrophosphorescence", Applied Physcis Letters, vol. 75, No. 1, Jul. 5, 1999, pp. 4-6.
Japan Society of Applied Physics, Organic Molecule Bioelectronics Section, Ninth Workshop, 17 (2001), pp. 17-22.
Japan Society of Applied Physics, Journal of Organic Molecule Bioelectronics Section, 14 (1), 23 (2003), 4 pages.
Hiroko Inomata, et al., "High-Efficiency Organic Electrophosphorescent Diodes Using 1,3,5-Triazine Electron Transport Materials", Chem. Mater. 2004, vol. 16, 2004, pp. 1285-1291.
Yuichiro Kawamura, et al., "100% phosphorescence quantum efficiency of Ir(III) complexes in organic semiconductor films", Applied Physics Letters, vol. 86., 2005, pp. 071104-1 to 071104-3.
Yuichiro Kawamura, et al., "Simple Accurate System for Measuring Absolute Photoluminescence Quantum Efficiency in Organic Solid-State Thin Films", Japanese Journal of Applied Physics , vol. 43, No. 11A, 2004, pp. 7729-7730.
Preprint of Organic El Symposium First Regular Meeting, 19 (2005), pp. 19-20.
U.S. Appl. No. 12/867,556, filed Aug. 13, 2010, Yokoyama, et al.
U.S. Appl. No. 12/865,736, filed Aug. 2, 2010, Yokoyama, et al.

* cited by examiner

*Primary Examiner* — Dawn L. Garrett
(74) *Attorney, Agent, or Firm* — Oblon, Spivak, McClelland, Maier & Neustadt, L.L.P.

(57) ABSTRACT

An object of the present invention is to provide a host compound in an emission layer, which has a high excited triplet level and completely confines triplet excitons of an phosphorescence-emitting substance. The invention relates to a compound containing an m-carbazolylphenyl group, which is represented by the following general formula (1):

[Chem. 1]

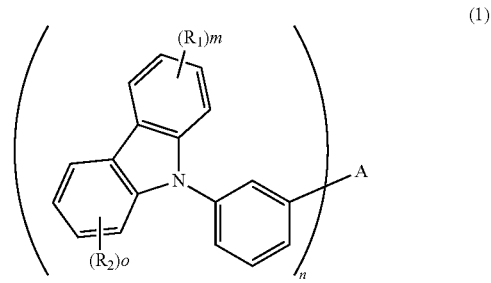

(1)

wherein A represents a nitrogen atom, an amino group to which a substituted or unsubstituted aromatic hydrocarbon group is bonded, a substituted or unsubstituted aromatic hydrocarbon group, a substituted or unsubstituted aromatic heterocyclic group, or a substituted or unsubstituted condensed polycyclic aromatic group; n represents an integer of 2 to 4; $R^1$ and $R^2$ may be the same or different and represent each an arbitrary substituent; and m and o represent each an integer of 0 to 4.

13 Claims, 7 Drawing Sheets

M-CARBAZOLYLPHENYL COMPOUNDS

TECHNICAL FIELD

The present invention relates to a compound containing an m-carbazolylphenyl group, suitable for an organic electroluminescence device which is a self-luminescent device suitable for various display devices. More specifically, it relates to a compound suitable for phosphorescence-emitting devices.

BACKGROUND ART

Since an organic electroluminescence device is a self-luminescent device, it is luminous, excellent in visibility, and capable of giving clear display, as compared with a liquid crystal device, so that active investigations have been made. Recently, as an approach to increase luminous efficiency of a device, a device that generates phosphorescence using a phosphorescence-emitting substance, that is, utilizes luminescence from a triplet-excited state, has been developed. According to the theory of an excited state, in the case of using phosphorescence emission, there is expected remarkable increase in luminous efficiency such that the luminous efficiency of about 4 times the conventional fluorescence emission becomes possible.

In 1993, M. A. Baldo et al. in Princeton University realized an external quantum efficiency of 8% by the use of a phosphorescence-emitting device using an iridium complex.

Since a phosphorescence-emitting substance induces concentration quenching, the substance is supported by doping a charge-transporting compound generally called a host compound therewith. The emitting substance to be supported is called a guest compound. As the host compound, 4,4'-di(N-carbazolyl)biphenyl (hereinafter referred to as CBP):

[Chem. 1]

has been used (see Non-Patent Document 1).

Non-Patent Document 1: Appl. Phys. Let., 75. 4 (1999)

However, since CBP has high crystallinity, it was pointed out to be poor in stability in a thin film state. For this reason, satisfactory device characteristics were not obtained in the case where heat resistance is required, for example, in the case of high luminance emission.

Therefore, 4,4',4''-tri(N-carbazolyl)triphenylamine (hereinafter referred to as TCTA):

[Chem. 2]

was proposed as a novel host compound and was confirmed to have luminous efficiency almost equal to that of CBP (see Non-Patent Document 2).

Non-Patent Document 2: Japan Society of Applied Physics, Organic Molecule Bioelectronics Section, Ninth Workshop, 17 (2001)

As the progress of the study on phosphorescence-emitting devices, elucidation of an energy transfer process between a phosphorescence-emitting device and a host compound was advanced and it was revealed that an excited triplet level of the host compounds should be higher than that of the phosphorescence-emitting device, so that there has been required a host material having an excited triplet level higher than that of CBP.

An external quantum efficiency of the phosphorescence-emitting device using, as a host compound in an emission layer, CBP doped with a blue phosphorescence-emitting substance Firpic:

[Chem. 3]

is still 6%. As a reason therefor, the excited triplet level of CBP is as low as 2.56 eV as compared with the excited triplet level of Firpic of 2.62 eV, so that it is considered that confinement of the excited triplet excitons of Firpic is insufficient.

This is evidenced by the fact that photoluminescence intensity of a CBP film doped with Firpic shows temperature dependency (see Non-Patent Document 3).

Non-Patent Document 3: Japan Society of Applied Physics, Journal of Organic Molecule Bioelectronics Section, 14(1), 23 (2003)

When the host compound in the emission layer is CBP, the confinement of the excited triplet excitons of Firpic is insufficient, so that non-radiating transition of the temperature dependency occurs and photoluminescence intensity decreases at room temperature.

Thus, in order to enhance luminous efficiency of a phosphorescence-emitting device, there has been required a host compound for the emission layer, which completely confines the triplet excitons of the phosphorescence-emitting device.

DISCLOSURE OF THE INVENTION

Problems to be Solved by the Invention

An object of the present invention is to provide a host compound in an emission layer, which has a high excited triplet level and completely confines triplet excitons of a phosphorescence-emitting substance. As physical characteristics of a compound suitable for the invention, there can be mentioned that (1) the excited triplet level is high, (2) intensity of photoluminescence of a film doped with a phosphorescence-emitting substance does not show temperature dependency, and (3) quantum efficiency of photoluminescence of a film doped with a phosphorescence-emitting substance is close to 100%.

Means for Solving the Problems

To achieve the above object, the present inventors have designed and chemically synthesized novel carbazole derivatives and explored the most suitable compound by investigating photoluminescence using the compounds and a phosphorescence-emitting substance to find out a novel compound having characteristics suitable for a phosphorescence-emitting device. Thus, the present invention has been completed.

Namely, the invention provides a compound for an organic electroluminescence device containing an m-carbazolylphenyl group, represented by the general formula (1):

[Chem. 4]

(1)

wherein A represents a nitrogen atom, an amino group to which a substituted or unsubstituted aromatic hydrocarbon group is bonded, a substituted or unsubstituted aromatic hydrocarbon group, a substituted or unsubstituted aromatic heterocyclic group, or a substituted or unsubstituted condensed polycyclic aromatic group; n represents an integer of 2 to 4; $R^1$ and $R^2$ may be the same or different and represent each an arbitrary substituent; and m and o each represent an integer of 0 to 4.

The substituted or unsubstituted aromatic hydrocarbon group in the amino group to which a substituted or unsubstituted aromatic hydrocarbon group is attached, the substituted or unsubstituted aromatic hydrocarbon group, the substituted or unsubstituted aromatic heterocyclic group, and the substituted or unsubstituted condensed polycyclic aromatic group, represented by Ar in the general formula (I), specifically include the following examples: a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a phenanthrolyl group, a furanyl group, a pyronyl group, a thiophenyl group, a quinolyl group, a benzofuranyl group, a benzothiophenyl group, an indolyl group, a carbazolyl group, a benzoxazolyl group, a quinoxalinyl group, a benzimidazolyl group, a pyrazolyl group, a dibenzofuranyl group, and a dibenzothiophenyl group.

A substituent in the substituted aromatic hydrocarbon group of the amino group to which a substituted aromatic hydrocarbon group is attached, the substituted aromatic hydrocarbon group, the substituted aromatic heterocyclic group, and the substituted condensed polycyclic aromatic group, represented by Ar in the general formula (I), specifically includes the following examples: a fluorine atom, a chlorine atom, a cyano group, a hydroxyl group, a nitro group, an alkyl group, an alkoxy group, a substituted or unsubstituted amino group, a trifluoromethyl group, a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a phenanthrolyl group, a furanyl group, a pyronyl group, a thiophenyl group, a quinolyl group, a benzofuranyl group, a benzothiophenyl group, an indolyl group, a carbazolyl group, a benzoxazolyl group, a quinoxalyl group, a benzimidazolyl group, a pyrazolyl group, a dibenzofuranyl group, and a dibenzothiophenyl group.

The arbitrary substituents represented by $R_1$ and $R_2$ in the general formula (1) specifically include the following examples: a fluorine atom, a chlorine atom, a cyano group, a hydroxyl group, a nitro group, an alkyl group, an alkoxy group, a substituted or unsubstituted amino group, a trifluoromethyl group, a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a phenanthrolyl group, a furanyl group, a pyronyl group, a thiophenyl group, a quinolyl group, a benzofuranyl group, a benzothiophenyl group, an indolyl group, a carbazolyl group, a benzoxazolyl group, a quinoxalyl group, a benzimidazolyl group, a pyrazolyl group, a dibenzofuranyl group, and a dibenzothiophenyl group.

Moreover, the invention is also characterized in that the compound containing an m-carbazolylphenyl group represented by the general formula (1) is a constitutional material in an emission layer or a hole transporting material, of an organic electroluminescence device. In the case of using the compound as a host material for a phosphorescence-emitting substance of a phosphorescence-emitting device, it provides an effect of improving luminous efficiency of the device.

Advantage of the Invention

The compound containing an m-carbazolylphenyl group of the invention has a high excited triplet level and completely confines triplet excitons of an phosphorescence-emitting substance, so that the compound is excellent as a host compound in an emission layer. Moreover, it is useful as a host compound in an emission layer or a hole transporting material, of an organic electroluminescence device, and thus a highly efficient and highly luminous organic electroluminescence device can be obtained by preparing an organic electroluminescence device using the compound.

BEST MODE FOR CARRYING OUT THE INVENTION

The compound containing an m-carbazolylphenyl group of the invention can be synthesized by condensing an arylamine and an aryl halide through Heck amination process, Ullmann reaction, or the like.

Of the compounds containing an m-carbazolylphenyl group represented by the general formula (1), specific examples of preferred compounds are shown below, but the invention is not limited to the compounds.

[Chem. 5]

(Compound 2)

[Chem. 6]

(Compound 3)

[Chem. 7]

(Compound 4)

[Chem. 8]

(Compound 5)

Purification of the compound of the invention can be conducted by purification through column chromatography, adsorption purification with various adsorbents, recrystallization with a solvent, or crystallization sublimation purification, and the like.

Identification of the compound of the invention can be conducted by NMR analysis and LC/MS analysis.

The excited triplet level of the compound of the invention was measured by the method described in Non-Patent Document 4 (see Non-Patent Document 4).

Non-Patent Document 4: Chem. Mat., 16, 1285 (2004)

Moreover, the temperature dependency of photoluminescence intensity of the compound of the invention was measured by the method described in Non-Patent Document 5 (see Non-Patent Document 5).

Non-Patent Document 5: Appl. Phys. Lett., 86(7), 1104 (2005)

The quantum efficiency of photoluminescence of the film wherein the compound of the invention is doped with a phosphorescence-emitting substance was measured by the method described in Non-Patent Document 6 (see Non-Patent Document 6).

Non-Patent Document 6: Jpn. J. Appl. Phys., 43, 7729 (2004)

The compound of the invention is suitably used as a host compound in an emission layer or as a hole transporting material, of an organic electroluminescence device. The device structure suitable for the organic electroluminescence device of the invention includes a structure comprising, successively on a substrate, an anode, a hole injecting layer, a hole transporting layer, an electron blocking layer, an emission layer, a hole blocking layer, an electron transporting layer, an electron injecting layer, and a cathode, or a structure comprising, successively on a substrate, an anode, a hole transporting layer, an emission layer, a layer serving as both hole blocking layer and electron transporting layer, an electron injecting layer, and a cathode. Furthermore, in these multilayered structures, several organic layers can be used in combination or can be omitted.

Concerning the emission layer, hole transporting layer, and electron transporting layer, each layer may have a structure wherein two or more layers are laminated.

Moreover, a hole injecting/transporting layer may be a P-doped hole injecting/transporting layer such as a polymeric material of N,N'-diphenyl-N,N'-di(m-tolyl)benzidine (hereinafter referred to as TPD) to which tristribromophenylamine hexachloroantimony is doped.

Furthermore, an electron injecting/transporting layer may be an N-doped electron injecting/transporting layer such as bathocuproin (hereinafter referred to as BCP) to which cesium is doped.

As the anode of the organic electroluminescence device of the invention, an electrode material having large work function, such as ITO or gold, is used. As the hole injecting layer, as well as copper phthalocyanine, materials such as naphthalene diamine derivatives and starburst type triphenyl amine derivatives or coating type materials can be used. As the hole transporting layer of the invention, as well as the compounds containing an m-carbazolyl group, TPD, N,N'-diphenyl-N, N'-di(α-naphthyl)benzidine (referred to as NPD), bis[N,N-di (p-tolyl)-4-aminophenyl]cyclohexane (referred to as TPAC), or the like can be used.

As the electron blocking layer of the organic electroluminescence device of the invention, compounds having electron blocking action, such as m-bis(N-carbazolyl)benzene (referred to as mCP), can be used.

The emission layer of the organic electroluminescence device of the invention is prepared by doping a hole injecting/transporting host material with a light-emitting substance called a guest material. The compound containing an m-carbazolylphenyl group represented by the general formula (I) of the invention can be used as a host material in the emission layer.

The guest material in the emission layer of the organic electroluminescence device of the invention may be a fluorescence-emitting substance or a phosphorescence-emitting substance. As the fluorescence-emitting substance, fluorescence-emitting substances such as rubrene derivatives, anthracene derivatives, and coumarin derivatives can be used. As the phosphorescence-emitting substance, green phosphorescence-emitting substances such as iridium complex of phenyl pyridine (Ir(Ppy)3), blue phosphorescence-emitting substances such as Firpic and Fir6, red phosphorescence-emitting substances such as Btp2Ir(acac), and the like can be used.

Since the guest material that is a phosphorescence-emitting substance induces concentration quenching, it is preferred to dope it by co-deposition in the range of 1 to 30% by weight relative to the whole emission layer.

Moreover, as described in Non-Patent Document 7, it is possible to prepare a device having a structure wherein a second emission layer prepared using a compound different in work function as a host material is neighbored (see Non-Patent Document 7).

Non-Patent Document 7: Preprint of Organic EL Symposium First Regular Meeting, 19 (2005)

As the hole blocking layer of the organic electroluminescence device of the invention, compounds having hole blocking action, such as phenanthroline derivatives including BCP and the like, aluminum (III) bis(2-methyl-8-quinolinate)-4-phenyl phenolate (hereinafter referred to as BAlq), oxadiazole derivatives, and triazole derivatives, are used.

As the electron transporting layer, oxadiazole derivatives, triazole derivatives, tris(8-hydroxyquinoline)aluminum which is an aluminum complex of quinoline (hereinafter referred to as Alq), and BAlq are used. As the electron injecting layer of the invention, there is, for example, lithium fluoride. However, in the preferred selection of the electron transporting layer and the cathode, this can be omitted. As the cathode, an electrode material having low work function, such as aluminum and an alloy of magnesium and silver, are used.

The embodiments of the invention will be illustrated in greater detail below with reference to Examples, but the invention is not limited to the following Examples so long as not exceeding its gist.

Example 1

Synthesis of tris[3-(carbazol-9-yl)phenyl]amine (Hereinafter Referred to as mTCTA) (Compound 2)

Figure 1:
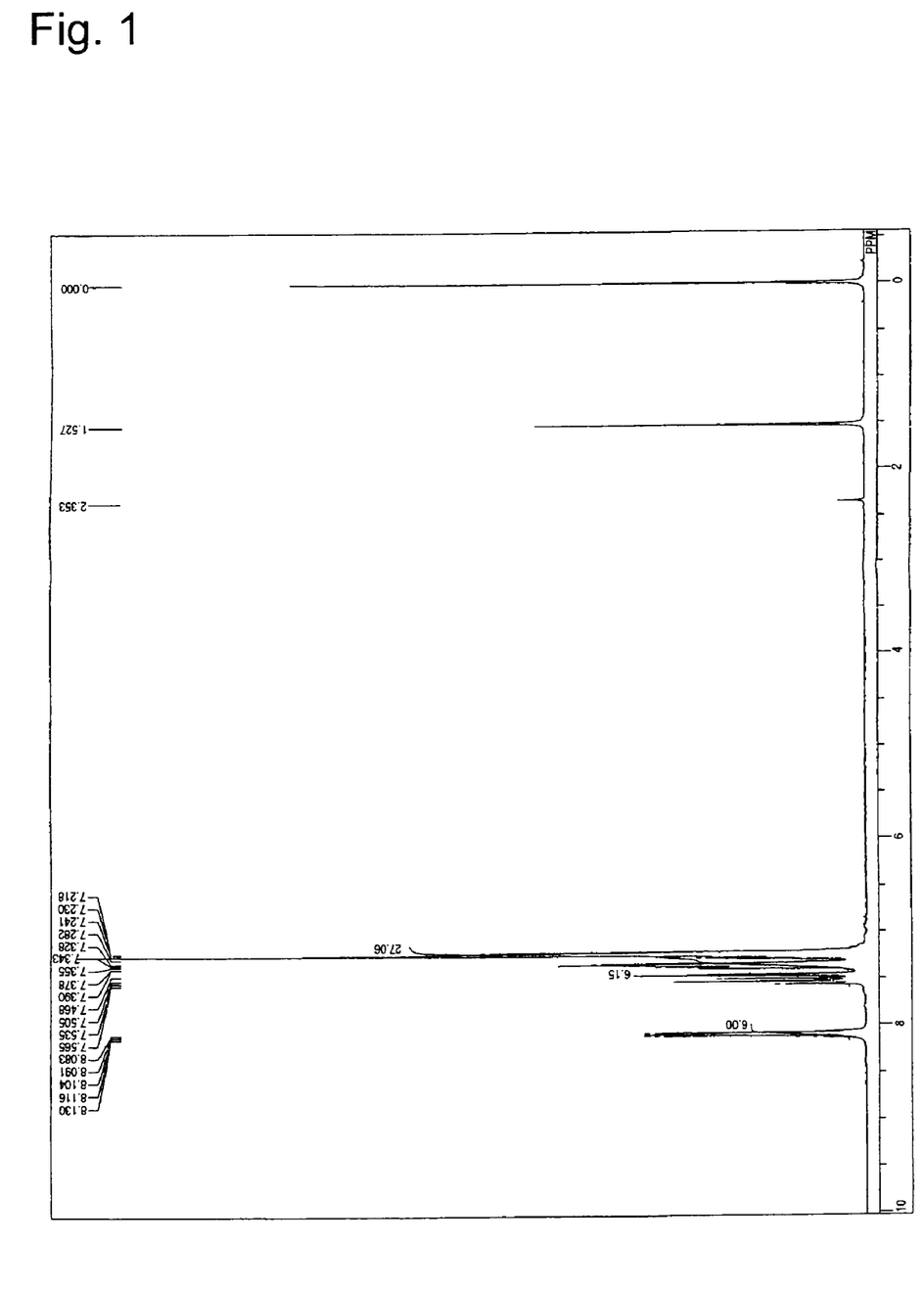
FIG. 1 is a chart of 1H-NMR of mTCTA (Compound 2).

5.5 g of bis[3-(carbazol-9-yl)phenyl]amine, 4.9 g of 9-(3-iodophenyl)carbazole, 2.1 g of sodium tert-butoxide, 0.1 g of palladium acetate, and 50 ml of anhydrous toluene were added in a flask under a nitrogen atmosphere. At an inner temperature of 71° C., 0.4 g of tert-butylphosphine was added by using a syringe. After 10 hours of reaction at 100° C., 300 ml of toluene was added to extract the objective substance, followed by filtration. The filtrate was concentrated to dryness to obtain a crude product. The dried crude product was purified by column chromatography to obtain 5.3 g (yield 56%) of mTCTA (Compound 2). The product was identified by 1H-NMR analysis (see FIG. 1). The following 36 hydrogen atoms were detected upon 1H-NMR (CDCl$_3$) analysis. δ (ppm): 8.083-8.130 ppm (6H), 7.468-7.565 ppm (6H), 7.128-7.390 ppm (24H).

Figure 2:
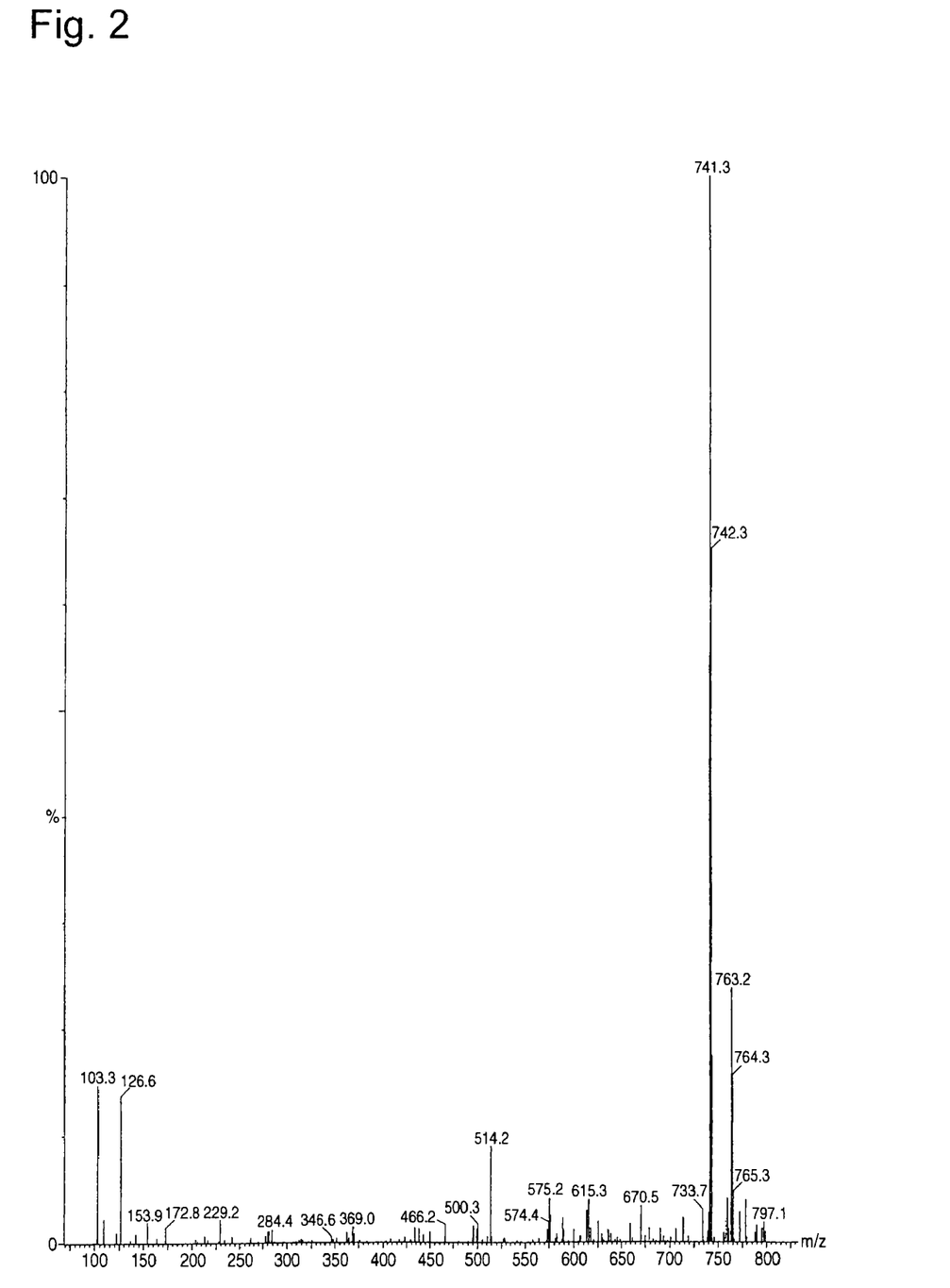
FIG. 2 is a chart of LC/MS of mTCTA (Compound 2).

Furthermore, molecular weight of the product was analyzed on LC/MS (2695 alliance/quatromicro API, the same shall apply hereinafter). The analytical values under proton addition conditions were 741.3 and 742.3, which were coincident with main molecular weights 740.3 and 741.3 of mTCTA (Compound 2) (see FIG. 2).

Example 2

Synthesis of N,N,N',N'-tetrakis[3-(carbazol-9-yl) phenyl]-4,4'-biphenyldiamine (Compound 3)

Figure 3:
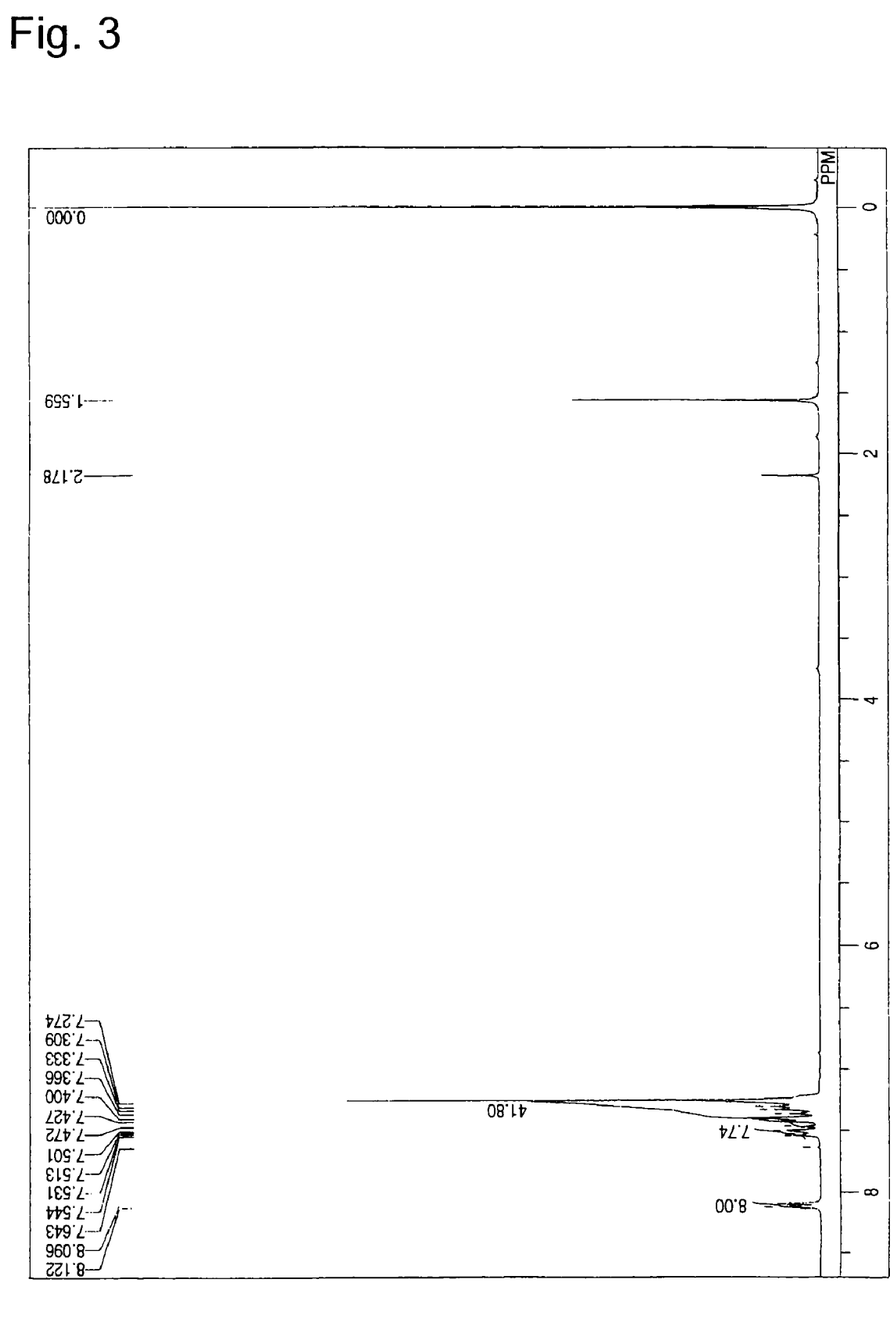
FIG. 3 is a chart of 1H-NMR of Compound 3.

1.50 g of bis[3-(carbazol-9-yl)phenyl]amine, 374 mg of 4,4'-dibromobiphenyl, 370 mg of sodium tert-butoxide, 12 mg of palladium acetate[II], and 10 ml of anhydrous toluene were added in a flask under a nitrogen atmosphere. At an inner temperature of 80° C., 42 mg of tert-butylphosphine was added by using a syringe. After 6 hours of reaction at 80° C., 50 ml of toluene was added to extract the objective substance, followed by filtration. The filtrate was concentrated to dryness to obtain a crude product. The dried crude product was purified by column chromatography to obtain 880 mg (yield 61%) of Compound 3 as a white solid. The product was identified by 1H-NMR analysis (see FIG. 3). The following 56 hydrogen atoms were detected upon 1H-NMR (CDCl$_3$) analysis. δ (ppm): 8.096-8.122 ppm (8H), 7.501-7.643 ppm (8H), 7.274-7.472 ppm (40H).

Further, the glass transition temperature, which is a measure of stability in an amorphous state, was 151.3° C.

Example 3

Synthesis of
1,3,5-tris[3-(carbazol-9-yl)phenyl]benzene
(Compound 4)

Figure 4:
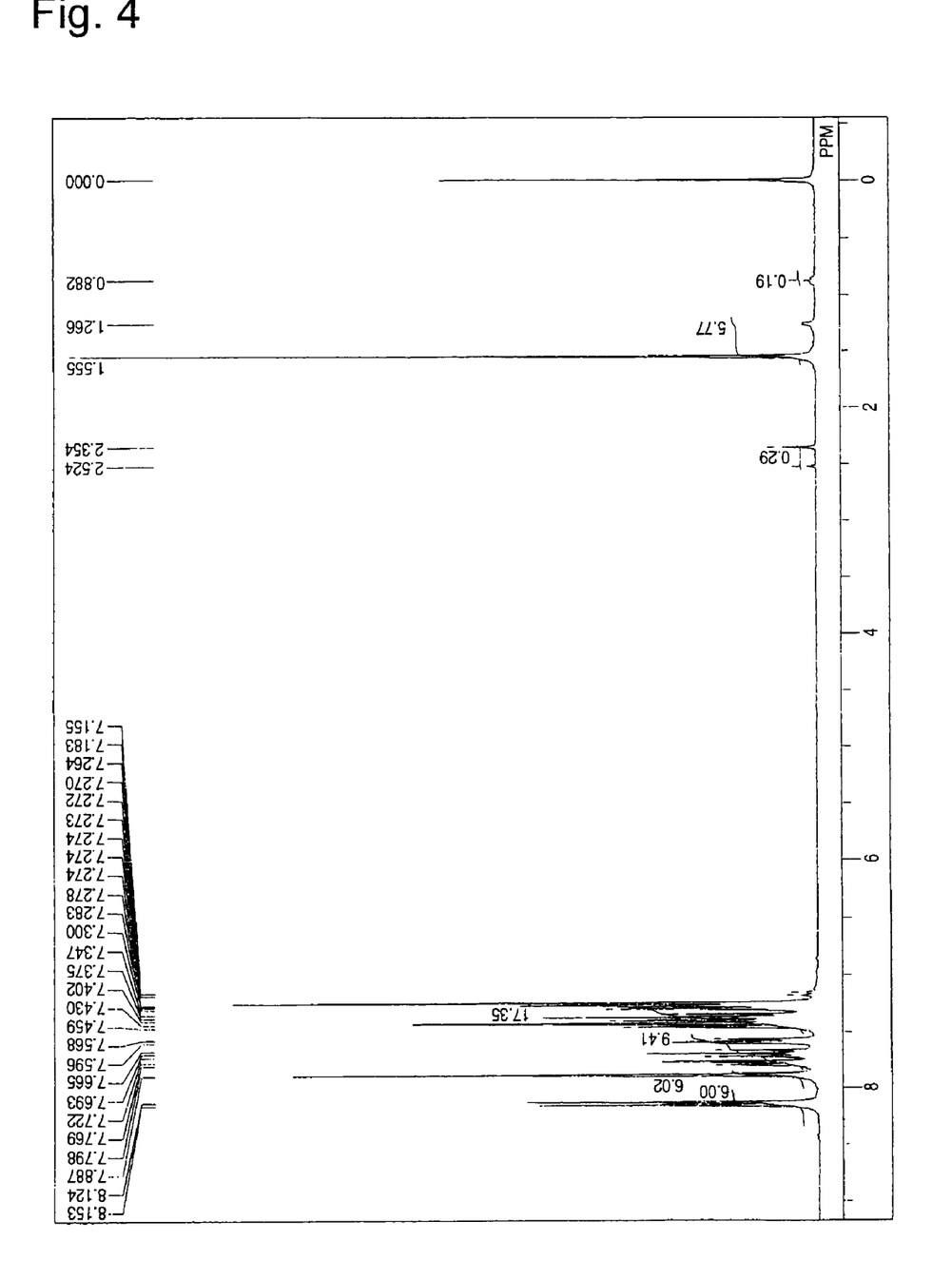
FIG. 4 is a chart of 1H-NMR of Compound 4.

1.00 g of 1,3,5-(3-bromophenyl)benzene, 1.00 g of carbazole, 38 mg of copper powder, and 1.10 g of potassium carbonate were added in a flask under a nitrogen atmosphere. After the whole was heated to an inner temperature of 170° C. and reacted for 20 hours, 50 ml of purified water was added thereto. After 1 hour of stirring at 90° C., insoluble matter was collected by suction filtration. After the insoluble matter was dissolved in tetrahydrofuran, copper powder was removed by suction filtration. The filtrate was concentrated to dryness to obtain a crude product. The dried crude product was purified by column chromatography to obtain 240 mg (yield 16.7%) of Compound 4 as a white solid. The product was identified by $^1$H-NMR analysis (see FIG. 4). The following 39 hydrogen atoms were detected upon $^1$H-NMR (CDCl$_3$) analysis. δ (ppm): 8.124-8.153 ppm (6H), 7.887 ppm (6H), 7.568-7.798 ppm (9H), 7.155-74590 ppm (18H). Further, the glass transition temperature, which is a measure of stability of an amorphous state, was 124.8° C.

Figure 5:
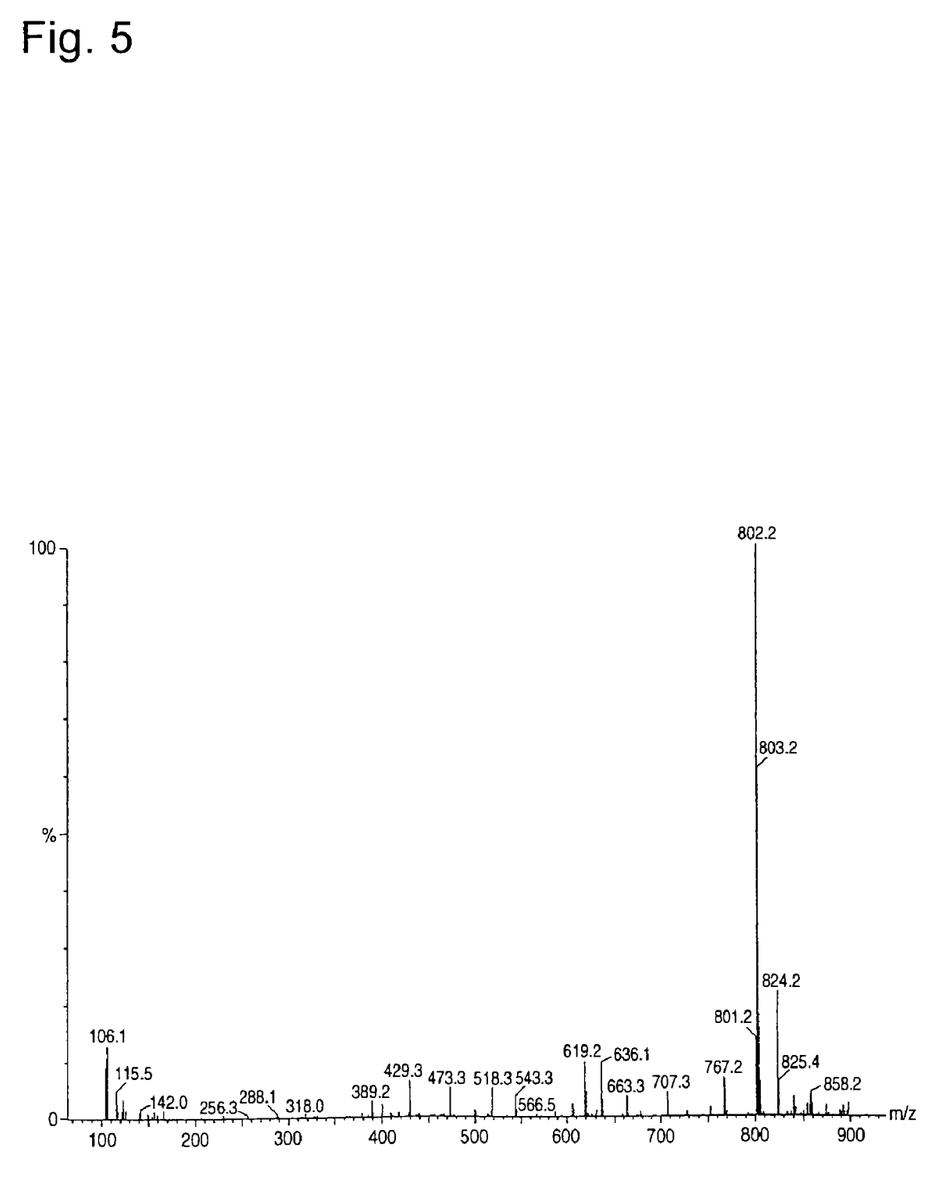
FIG. 5 is a chart of LC/MS of Compound 4.

Furthermore, molecular weight of the product was analyzed on LC/MS. The analytical values under proton addition conditions were 802.2 and 803.2, which were coincident with main molecular weights 801.3 and 802.3 of Compound 4 (see FIG. 5).

Example 4

Figure 6:
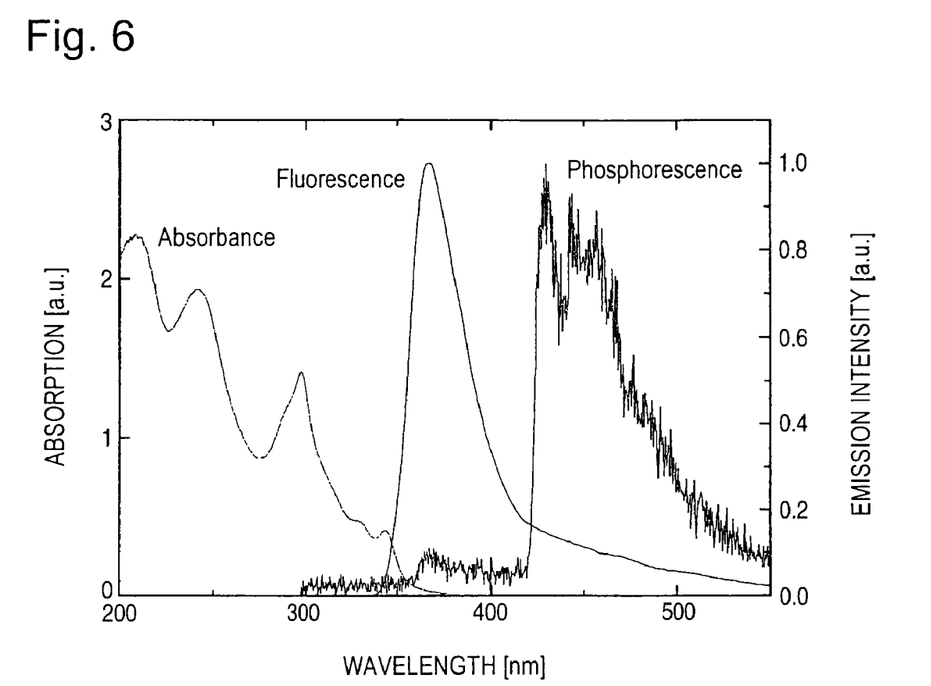
FIG. 6 is a chart of absorption, fluorescence, and phosphorescence spectra of mTCTA (Compound 2).
Figure 7:
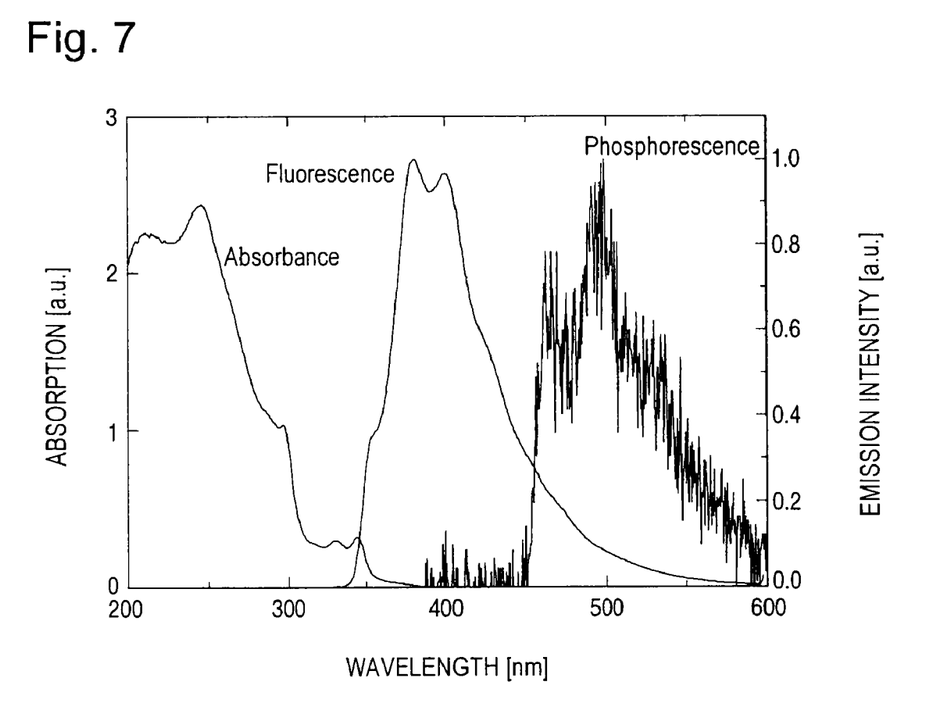
FIG. 7 is a chart of absorption, fluorescence, and phosphorescence spectra of Compound 4.
Figure 8:
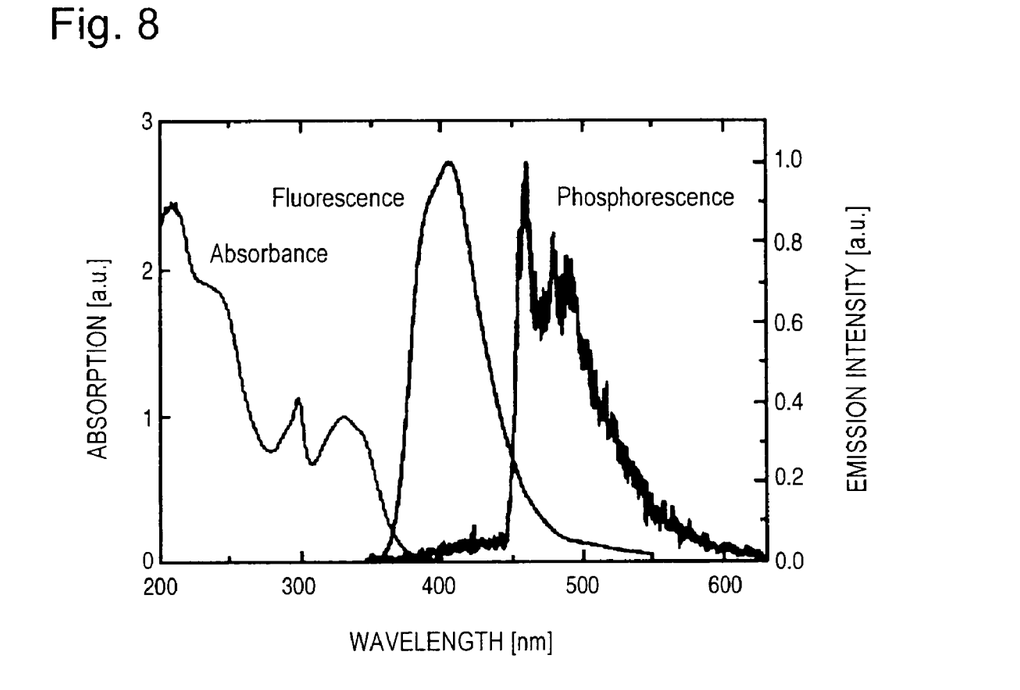
FIG. 8 is a chart of absorption, fluorescence, and phosphorescence spectra of mTCTA (Comparison).

Using a streak camera (manufactured by Kyushu University, the same shall apply hereinafter), phosphorescence spectra at the time when laser irradiation at 325 nm was applied to a thin film of 100 nm at 5K were observed for mTCTA (Compound 2), Compound 4, and TCTA as a reference (see FIGS. 6 to 8). Short-wave peaks of the phosphorescence spectra were as follows and thus it was confirmed that the compound of the invention was shifted to a short-wave side.
mtCTA (Compound 2)
Phosphorescence peak wavelength: 429.7 nm (FIG. 6)
Compound 4
Phosphorescence peak wavelength: 462.0 nm (FIG. 7)
TCTA
Phosphorescence peak wavelength: 460.7 nm (FIG. 8)
The above peak wavelengths were converted to light energy to determine excited triplet levels.

| | |
|---|---|
| mTCTA (Compound 2) | triplet level: 2.89 eV |
| Compound 4 | triplet level: 2.69 eV |
| TCTA | triplet level: 2.69 eV |

The excited triplet level is higher than 2.56 eV of CBP and, in order to confine triplet excitons of Firpic having an excited triplet level of 2.62 eV, it was revealed that the compounds of the invention having a high excited triplet level were suitable.

Example 5

Figure 9:
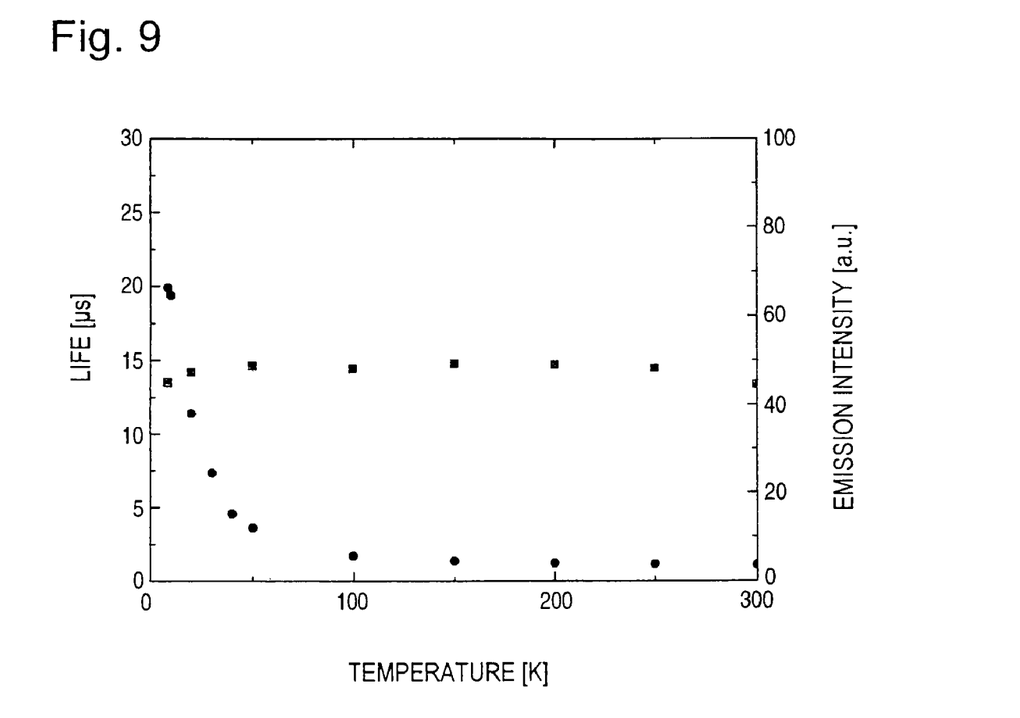
FIG. 9 is a graph showing temperature dependency of phosphorescence intensity (■) and phosphorescence life (●) of Firpic.

In order to investigate suitability of mTCTA (Compound 2) as a host compound in an emission layer, Firpic was co-deposited in an amount of 6% by weight to prepare a thin film of 100 nm. Using the streak camera, temperature dependency of phosphorescence intensity at the time when laser irradiation was applied to a thin film of 100 nm in the range of 5K to 300K was observed (see FIG. 9). Since no temperature dependency was observed on the phosphorescence intensity, it was confirmed that the compound of the invention completely confined the triplet excitons of Firpic.

Example 6

In order to investigate suitability of mTCTA (Compound 2) as a host compound in an emission layer, Firpic was co-deposited in an amount of 6% by weight to prepare a thin film of 100 nm. Using an integrating sphere (manufactured by Kyushu University), phosphorescence quantum efficiency of Firpic at the time when laser irradiation at 325 nm was applied was measured. The phosphorescence quantum efficiency was 100% (error 5%). Since the phosphorescence quantum efficiency of Firpic is coincident with a theoretical value thereof, it was confirmed that the compound of the invention preferably transmitted irradiation energy to the phosphorescence-emitting substance Firpic and completely confined triplet excitons of the phosphorescence-emitting substance, as a host compound in an emission layer, to exhibit the highest luminous efficiency.

From the above results, the compounds of the invention have a high excited triplet level, preferably transmit irradiation energy to the phosphorescence-emitting substance, and completely confine triplet excitons of the phosphorescence-emitting substance, so that the compounds are excellent as a host compound in an emission layer.

While the invention has been described in detail and with reference to specific embodiments thereof, it will be apparent to one skilled in the art that various changes and modifications can be made therein without departing from the spirit and scope thereof.

The present application is based on Japanese Patent Application No. 2005-357634 filed on Dec. 12, 2005, and the contents are incorporated herein by reference.

INDUSTRIAL APPLICABILITY

The compound containing an m-carbazolylphenyl group of the present invention has a high excited triplet level and completely confines triplet excitons of the phosphorescence-emitting substance, so that the compound is excellent as a host compound in an emission layer. Moreover, by preparing an organic electroluminescence device using the compound, luminance and luminous efficiency of conventional organic electroluminescence devices can be remarkably improved and therefore performance of mobile electronic products can be improved.

The invention claimed is:
1. A compound containing an m-carbazolylphenyl group, which is represented by the general formula (1):

[Chem. 1]

wherein A represents a nitrogen atom, an amino group to which a substituted or unsubstituted aromatic hydrocarbon group is bonded, a substituted or unsubstituted aromatic heterocyclic group, or a substituted or unsubstituted condensed polycyclic aromatic group; n represents an integer of 2 to 4; $R_1$ and $R_2$ may be the same or different and represent each an arbitrary substituent; and m and o each represent an integer of 0 to 4.

2. The compound according to claim 1 for an organic electroluminescence device.

3. The compound according to claim 1, which is used as a host compound in an emission layer or a hole transporting material, of an organic electroluminescence device.

4. The compound according to claim 1, which is used as a host material for a phosphorescence-emitting substance of a phosphorescence-emitting device.

5. An organic electroluminescence device comprising at least a hole transporting layer and an emission layer, wherein the hole transporting layer or the emission layer contains the compound according to claim 1.

6. The organic electroluminescence device according to claim 5, wherein the compound is contained as a host material in the emission layer.

7. The organic electroluminescence device according to claim 6, wherein the guest material in the emission layer is a fluorescence-emitting substance or a phosphorescence-emitting substance.

8. The organic electroluminescence device according to claim 7, wherein the guest material is a phosphorescence-emitting substance.

9. A compound which is at least one compound selected from the group consisting of and -continued 10. The organic electroluminescence device according to claim 6, wherein said emission layer comprise a fluorescence-emitting substance which is a rubrene derivative.

11. The organic electroluminescence device according to claim 6, wherein said emission layer comprise at least one phosphorescence-emitting substance which is selected from the group consisting of an iridium complex of phenyl pyridine, FIrpic, FIr6 and $Btp_2Ir(acac)$.

12. The organic electroluminescence device according to claim 8, wherein said guest material is present in an amount of 1 to 30 wt % relative to the whole emission layer.

13. The organic electroluminescence device according to claim 5, wherein said hole transporting layer contains the compound according to claim 1.

* * * * *